(12) United States Patent
Brown et al.

(10) Patent No.: US 7,507,852 B2
(45) Date of Patent: Mar. 24, 2009

(54) PROCESS FOR PREPARING GAMMA-CYHALOTHRIN

(75) Inventors: Stephen Martin Brown, Huddersfield (GB); Brian David Gott, Huddersfield (GB)

(73) Assignee: Syngenta Limited (GB)

( * ) Notice: Subject to any disclaimer, the term of this patent is extended or adjusted under 35 U.S.C. 154(b) by 453 days.

(21) Appl. No.: 10/546,138

(22) PCT Filed: Feb. 23, 2004

(86) PCT No.: PCT/GB2004/000726

§ 371 (c)(1), (2), (4) Date: Aug. 19, 2005

(87) PCT Pub. No.: WO2004/074237

PCT Pub. Date: Sep. 2, 2004

(65) Prior Publication Data

US 2006/0148892 A1    Jul. 6, 2006

(30) Foreign Application Priority Data

Feb. 24, 2003    (GB) ................................ 0304132.4

(51) Int. Cl.
*C07C 253/30*    (2006.01)

(52) U.S. Cl. .................................................... 558/410
(58) Field of Classification Search ................ None
See application file for complete search history.

(56) References Cited

U.S. PATENT DOCUMENTS

| 4,252,820 A | 2/1981 | Lantzsch et al. |
| 5,164,411 A | 11/1992 | Baum et al. |

FOREIGN PATENT DOCUMENTS

| EP | 0109681 | 5/1984 |
| EP | 0304954 | 3/1989 |
| WO | WO 02/06202 | 1/2002 |

OTHER PUBLICATIONS

Bentley P D et al: Fluorinated Analgoues of Chrysanthemic Acid; Pesticide Science, Elsevier Applied Science Pub., vol. 11, No. 2, 1980, pp. 156-164.

*Primary Examiner*—Kamal A Saeed
(74) *Attorney, Agent, or Firm*—Rebecca A. Howard

(57) ABSTRACT

A process for the preparation of gamma-cyhalothrin comprising steps of a) chlorinating 1R cis-Z 3-(2-chloro-3,3,3-trifluoro-1-propenyl)-2,2-dimethyl cyclopropanecarboxylic acid to give 1R cis-Z 3-(2-chloro-3,3,3-trifluoro-1-propenyl)-2,2-dimethyl cyclopropanecarboxylic acid chloride and b) esterifying 1R cis-Z 3-(2-chloro-3,3,3-trifluoro-1-propenyl)-2,2-dimethyl cyclopropanecarboxylic acid chloride with the (S)-cyanohydrin of 3-phenoxy benzaldehyde (III).

7 Claims, No Drawings

PROCESS FOR PREPARING GAMMA-CYHALOTHRIN

This application is a 371 of International Application No. PCT/GB2004/000726 filed Feb. 23, 2004, which claims priority to GB 0304132.4, filed Feb. 24, 2003, the contents of which are incorporated herein by reference.

The present invention relates to a process for making insecticidal cyclopropanecarboxylic acid esters. More particularly, the invention relates to a process for making gamma-cyhalothrin [(S)-α-cyano-3-phenoxybenzyl (Z)-(1R,3R)-3-(2-chloro-3,3,3-trifluoro-1-propenyl)-2,2-dimethylcyclopropanecarboxylate].

It is well known that the insecticidal activity of pyrethroids such as cyclopropanecarboxylic acid esters e.g. cyhalothrin is greatly affected by their stereochemistry. It is disclosed in Bentley et al, Pestic. Sci. (1980), 11(2), 156-64) that (S)-α-cyano-3-phenoxybenzyl (Z)-(1R,3R)-3-(2-chloro-3,3,3-trifluoro-1-propenyl)-2,2-dimethylcyclopropanecarboxylate is the most active isomer of cyhalothrin.

In order to produce gamma-cyhalothrin on an industrial scale it is desirable to find methods of making the final product that avoid the use of expensive reagents and have as few chemical stages as possible. The present invention provides a direct process to meet these requirements. There is therefore provided a process for the preparation of gamma-cyhalothrin (IV) comprising a) chlorinating 1R cis-Z 3-(2-chloro-3,3,3-trifluoro-1-propenyl)-2,2-dimethyl cyclopropanecarboxylic acid (I) to give 1R cis-Z 3-(2-chloro-3,3,3-trifluoro-1-propenyl)-2,2-dimethyl cyclopropanecarboxylic acid chloride (II) and b) esterifying 1R cis-Z 3-(2-chloro-3,3,3-trifluoro-1-propenyl)-2,2-dimethyl cyclopropanecarboxylic acid chloride (II) with the (S)-cyanohydrin of 3-phenoxy benzaldehyde (III).

1R cis-Z 3-(2-chloro-3,3,3-trifluoro-1-propenyl)-2,2-dimethyl cyclopropanecarboxylic acid (I) is a known compound and its preparation is described for example in U.S. Pat. No. 4,683,089, WO02/06202, WO97/03941 and WO/9942432.

Step a) is performed by standard techniques as in '*March 4th Edition*-p 437-38'. Preferred chlorinating agents are thionyl chloride, phosgene or phosphorous oxychloride. Preferred solvents are hydrocarbons such as toluene, hexane, heptane or fluorobenzene. Preferred temperatures are from ambient to 100° C. or the boiling point of the solvent.

Preferably the acid (I) has an enantiomeric purity of greater than 80% of 1R 3R enantiomer, and more preferably greater than 90% 1R 3R enantiomer.

Step b) is performed in the presence of a solvent or in the absence of a solvent, in which case the molten product can act as the reaction medium. The reaction can be carried out in a single organic phase or in a mixture of a water immiscible organic phase and an aqueous phase. The acid chloride, either neat or in a solvent, may be added to the cyanohydrin, or the vice versa, but it is preferable to add the acid chloride to the cyanohydrin. The mol ratio of the reactants is preferably 1:1 but up to 10 mol % excess of either reactant can be employed, but most preferably the excess of one reactant over the other is 1-5 mol %.

On an industrial scale it is highly desirable that the reaction is taken to completion (where, in the case of 1:1 stoichiometry of reactants, completion means there is a residual level of both acid chloride and cyanohydrin of <5% by weight and preferably <1% by weight, and where one reactant is used in excess of the other, the residual level of the minor reactant is <1% preferably <0.2%) to maximize the yield.

In known esterification processes for making other pyrethroids (e.g. EP109681, U.S. Pat. No. 4,252,820, EP3336A1, U.S. Pat. No. 4,258,202, WO0206202, GB2000764, U.S. Pat. No. 4,343,677 and U.S. Pat. No. 5,164,411) taking the reaction to completion has not been attempted or has been attempted either by performing the reaction in the presence of a stoichiometric amount of an organic base (e.g. U.S. Pat. No. 4,258,202) or by physical removal of the HCl as it is formed by conducting the reaction at the boiling point of the solvent (e.g. U.S. Pat. No. 5,164,411). However neither of these processes is satisfactory. The use of stoichiometric amounts of a base is undesirable as this necessitates a complicated recovery process to avoid the cost of disposing of the base. When using physical removal of HCl as a means of progressing the esterification reaction, the applicants have found that it is difficult to consume the last few % of the reactants without significantly extending the reaction time. Surprisingly the reaction can be taken to completion within an acceptable time by removal of HCl from the reaction using a combination of physical methods and a sub-stoichiometric amount of a base.

Therefore in one aspect of the invention there is provided a process in which HCl formed during the esterification is removed from the reaction mass using a combination of physical methods and a sub-stoichiometric amount of a base.

Physical removal of co-product HCl can be accomplished by conducting the reaction at the boiling point of the solvent or by continuous removal of the solvent by distillation whilst adding fresh solvent to replace that which has been distilled out or by application of vacuum or by sparging the reaction mass with an inert gas such as nitrogen or by the presence of a separate water phase that can extract the HCl, or by any combination of these procedures. The base can be either an organic base, such as a tertiary amine, or an inorganic base such as an alkali metal carbonate or bicarbonate or alkaline earth metal oxide, hydroxide or carbonate or a combination of an organic and an inorganic base. In the latter case, the organic base serves to facilitate the reaction of the HCl formed in the reaction with the heterogeneous inorganic base.

The base may be added from the outset or may be added during the course of the reaction but is preferably added once the reaction has been taken to >50% by physical removal of HCl and most preferably after the reaction is >80% completed.

The applicants have found that addition of the base late on in the reaction has the advantage of minimising impurity formation and maximizing yield.

Preferred organic bases have a pKa of between 2 and 7 and more preferably between 3 and 6. Particularly preferred organic bases are pyridine, alkylpyridines, quinoline, the trimethylether of triethanolamine or the mono-hydrochloride salt of DABCO (1,4-diazabicyclo[2.2.2]octane). The base can be used at <0.8 equivalents on the acid chloride, preferably <0.5 equivalents and most preferably between 0.1-0.25 equivalents. When an organic and an inorganic base are combined, it is desirable to have the inorganic base as the major component of the binary mixture and the organic base as the minor component. Thus the organic base is preferably <50% and most preferably <10% of the total molar amount of base used in the reaction.

Suitable solvents for the reaction are aliphatic or aromatic hydrocarbons. Examples of aromatic hydrocarbons are toluene, o-xylene, mixed xylenes or halobenzenes, for example fluorobenzene. Aliphatic hydrocarbons are for example hexane, cyclohexane, iso-hexane, heptane, octane or mixtures of hydrocarbons commonly known as petroleum ethers. Preferred solvents are hexane, cyclohexane, iso-hexane, heptane or octane.

In a preferred embodiment of the invention, the same solvent is used in both steps a) and b). Suitable temperatures for the reaction are in the range 20-120° C., preferably 60-80° C.

In a further aspect of the invention, the esterification can be carried out in a two-phase system in which one phase is an aqueous phase and optionally in the presence of an organic base that may act as a reaction promoter. The aqueous phase serves to help extract the HCl as it forms from the organic phase and the pH of the aqueous phase can be maintained at a desired level by addition of base to neutralize the HCl as it forms. The preferred pH of the aqueous phase is pH 3-10 but preferably pH 6-8. The pH can be maintained by continuous addition of an inorganic base, for example sodium or potassium hydroxide, and the use of a 'pH stat', which will control the pH automatically. The pH control is optionally carried out in the presence of a buffer, which helps to avoid large swings in the pH. Suitable buffers are borate or phosphate salts. Suitable reaction promoters are organic bases such as pyridine or alkyl pyridines.

On completion of the reaction, any base, along with salts formed in the reaction, can be removed by washing the product with dilute mineral acid. Optionally this can be carried out at elevated temperature to hydrolyse any residual acid chloride, or any acid anhydride formed in the reaction, to the carboxylic acid. The carboxylic acid can then be removed from the product by washing with water that has a pH maintained in the region of pH 5-8 and preferably pH 6-7. This can be accomplished by the use of an appropriate buffer and controlled addition of a base, for example sodium or potassium dihydrogen phosphate and sodium or potassium hydroxide. Finally, the product is washed with dilute acid to prevent epimerisation at the benzylic position and any solvent is removed by conventional methods. The product can then be purified further if required by, for example, recrystallisation.

Alternatively, the product can be crystallised directly from the reaction solvent. In this case, the preferred reaction solvents are aliphatic hydrocarbons. In a preferred embodiment of the invention, the same solvent is used in steps a) and b) of the process and in the final purification.

The following Examples illustrate the invention.

The products were analysed by Gas Chromatography using an Agilent gas chromatograph with a Chrompack CP Sil 5 CB column (50 metres, 0.32 mm ID and 0.1 μm film thickness) with helium as carrier, split injection at 15 psi. Injection temperature 300° C. detector 325° C. and a detector gas composition of hydrogen 30 ml/min, air 350 ml/min and helium at 30 ml/min). The oven temperature profile was: initial temp 50° C., initial time 6 mins then heating rate 10° C. min to 120° C. and hold for 3 mins then ramp to 240° C. at 25° C./min. Hold for 8 minutes then ramp to 300° C. at 50° C. and hold for 6 minutes to burn off the column.

Using these conditions, the following retention times were observed:

(S)-α-cyano-3-phenoxybenzyl (Z)-(1R,3R)-3-(2-chloro-3,3,3-trifluoro-1-propenyl)-2,2-dimethylcyclopropanecarboxylate (gamma-cyhalothrin) 27.4 mins (R)-α-cyano-3-phenoxybenzyl (Z)-(1R,3R)-3-(2-chloro-3,3,3-trifluoro-1-propenyl)-2,2-dimethylcyclopropanecarboxylate 27.0 mins

EXAMPLE 1

Preparation of 1R cis-Z 3-(2-chloro-3,3,3-trifluoro-1-propenyl)-2,2-dimethyl-cyclopropane carboxylic acid chloride A 1 liter dry, clean jacketed split reaction vessel equipped with agitator, thermometer, condenser, nitrogen blanket and vent to a scrubber system was charged with toluene (450 ml) and agitated whilst 1R cis-Z 3-(2-chloro-3,3,3-trifluoro-1-propenyl)-2,2-dimethyl-cyclopropane carboxylic acid (89.4 gm=0.369 mol) was added followed by triethylamine (0.21 gm=2.1 mmol). The reaction mixture was then heated to 45° C., using oil circulation on the jacket, and thionyl chloride (62.0 gm=0.52 mol) was then charged over 105 minutes maintaining on temperature. The reaction mass was then agitated for 5 hours at 45° C. then tested by GLC for completion of reaction showing 2% residual acid. A further addition of thionyl chloride (4.4 gm=37 mmol) was then made and the reaction mass allowed to cool with stirring overnight. The following day, residual thionyl chloride, dissolved sulphur dioxide and hydrogen chloride gases were removed by distillation of about 320 ml toluene under vacuum. GC, GCMS and NMR analysis of the product were consistent with the structure of the acid chloride (IIIa). Yield, 175 gm of a 54% solution of the acid chloride in toluene, 97% theory. $\alpha_D$=+46° (c=0.012, DCM).

EXAMPLE 2

Thermal Coupling of ((1R,3S)-3-((Z)-2-Chloro-propenyl)-2,2-dimethyl-cyclopropanecarbonyl chloride to (S)-3-phenoxybenzaldehyde cyanohydrin with distillative removal of HCl and completion with pyridine The acid chloride (II) (5 gm 23 millimol) and cyclohexane (25 ml) were added to a dry 100 ml 3 necked round bottomed flask fitted with magnetic stirrer bar, short path distillation equipment (vented to a caustic scrubber system), thermometer and nitrogen blanket. The reactor contents were agitated and heated to 80° C. Distillation was started and the S-cyanohydrin (5.06 gm @ 90%=20 millimol), dissolved in a little cyclohexane, was then added over approximately 1 hour. Cyclohexane was then continually added at the same rate as the loss of cyclohexane by distillation. After 3.5 hours, GC analysis showed that most of the acid chloride had been consumed. A further charge of acid chloride was made (0.35 gm 1.3 millimol) and the reaction mixture allowed to cool and stir overnight. A further addition of acid chloride (0.7 gm 2.6 millimol) was made and refluxing continued for 21 hrs after which time there was still 1.9 area % acid chloride in the reaction mass.

Pyridine (0.05 gm 0.6 millimol) and S-cyanohydrin were added (0.314 gm 1.3 millimol), and the reaction mass was refluxed for 3 hrs then allowed to cool to room temperature. GC analysis showed the acid chloride level to be 0.1%. The reaction mass was then worked up by the addition of hexane (40 ml) which promoted crystallisation on stirring. The resultant white solid was separated from the solvent by filtration and washed with hexane (2×5 ml), water (5 ml) and hexane (5 ml) and pulled dry to give a white solid (1.4 gm). The organic phase was washed with 2 molar hydrochloric acid (20 ml), water (20 ml) and brine (20 ml). Both the solid product and organic phase were then analysed by GC. The product in both solid form and in solvent solution had a ratio of (S)-α-cyano-3-phenoxybenzyl (Z)-(1R,3R)-3-(2-chloro-3,3,3-trifluoro-1-propenyl)-2,2-dimethylcyclopropanecarboxylate to (R)-α-cyano-3-phenoxybenzyl (Z)-(1R,3R)-3-(2-chloro-3,3,3-trifluoro-1-propenyl)-2,2-dimethylcyclopropanecarboxylate of 95:5.

EXAMPLE 3

Thermal Coupling of ((1R,3S)-3-((Z)-2-Chloro-propenyl)-2,2-dimethyl-cyclopropanecarbonyl chloride to (S)-3-phenoxybenzaldehyde cyanohydrin with distillative removal of HCl The S-cyanohydrin (1 gm @ 90%=4 millimol) was charged to a clean dry 3 necked round bottomed flask fitted with magnetic stirrer bar, short path distillation equipment (vented to a caustic scrubber system), thermometer and nitrogen blanket.

Cyclohexane (15 to 20 ml) was then added to the reactor agitation and the nitrogen blanket started at 20° C. The S-cyanohydrin was a slurry in the system at this temperature. The slurry was agitated and heated 80° C. until the cyclohexane started to distil. At this point the acid chloride (1.24 gm 4.8 millimol) dissolved in cyclohexane (15 ml) was added, dropwise, to the reactor over 1 hour trying to balance the addition rate with the cyclohexane distillation rate. The addition of the acid chloride was sub-surface via a syringe pump fitted with a Teflon syringe. Once the addition was complete the distillation was continued replacing the distilled cyclohexane with fresh solvent. Reaction progress was monitored by GC. After completion of addition, there was 29 area % acid chloride, 24 area % cyanohydrin and 44 area % gamma-cyhalothrin present (96:4 ratio of α-S to α-R diastereomers). After 2.5 hours a further addition of S-cyanohydrin (0.1 gm=0.4 millimol) was made and the distillation continued for a further 1 hr after which time there was still 7.3 area % acid chloride remaining. The reaction mass was then cooled to room temperature and left, without agitation, overnight under nitrogen. The following day the reaction mass was re-heated to 80° C. and a further addition of S-cyanohydrin (0.1 gm=0.4 millimol) made followed by 3 hours of distillative reaction and finally cooling and bottling off. Analysis of the reaction showed that the diastereoisomer ratio was 95:5.

EXAMPLE 4

Further runs were performed and the results are given in Table I.

TABLE I

Coupling of ((1R,3S)-3-((Z)-2-Chloro-propenyl)-2,2-dimethyl-cyclopropanecarbonyl chloride with (S)-3-phenoxybenzaldehyde cyanohydrin

| Experiment Number | Scale mmol Acid Chloride | Solvent | Base/Buffer (Base mol ratio) | Reaction Temp ° C. | Mode of addition and reaction times | End of reaction Acid Chloride Area % | Product Diastereo-isomer Ratio |
|---|---|---|---|---|---|---|---|
| 1 | 7.74 | Toluene | Pyridine (1:1) | −10° C. | Acid chloride added to cyanohydrin and then base added. 4 hrs after addition 88% complete. | 0 | 92.8 |
| 2 | 2.14 | Toluene | Pyridine (1:1) | −10° C. | Acid chloride added to cyanohydrin and then base added. 4 hrs after addition 87% complete. | 0 | 92.5 |
| 3 | 19.1 | Toluene | Pyridine (1:1) | −10° C. | Slow base addition to acid chloride + cyanohydrin. 4 hrs after addition 90% complete. | 0 | 95.5 |
| 4 | 10.7 | Toluene | Pyridine (1:1) | −10° C. | Co-addition of acid chloride & base to cyanohydrin. Reaction 83% complete after 2 hrs. | 0.3 | 95.4 |
| 5 | 21 | Water | NaOH/phosphate | 10° C. | Co-addition of cyanohydrin and acid chloride with aqueous controlled at pH 7 ± 1. Worked up after 1 hr 16.8% complete. | 6.8 | 92.9 |

TABLE I-continued

Coupling of ((1R,3S)-3-((Z)-2-Chloro-propenyl)-2,2-dimethyl-cyclopropanecarbonyl chloride with (S)-3-phenoxybenzaldehyde cyanohydrin

| Experiment Number | Scale mmol Acid Chloride | Solvent | Base/Buffer (Base mol ratio) | Reaction Temp ° C. | Mode of addition and reaction times | End of reaction Acid Chloride Area % | Product Diastereo-isomer Ratio |
|---|---|---|---|---|---|---|---|
| 6 | 21 | Hexane/water | NaOH/phosphate | 10° C. | Co-addition of cyanohydrin and acid chloride with aqueous controlled at pH 7 ± 1. Worked up after 1 hr 5.3% complete. | 20.7 | 88.7 |
| 7 | 152 | Hexane/water | Sodium tetra-borate (1.5) | 10° C. | Co-addition of cyanohydrin and acid chloride with aqueous at pH 9. Only 17.1% complete after 2 hrs. | 0.1 | 92.6 |
| 8 | 20 | Hexane/water | NaOH | 10° C. | Co-addition of cyanohydrin and acid chloride with aqueous controlled at pH 13. Worked up after 5 hrs 29.5% complete. | 27.4 | 44.4 |
| 9 | 2.37 | Toluene | None | 75° C. | Reactants charged and heated to 75° C. and stirred overnight sampling regularly. Worked up after 24 hrs 34.5% complete. | 30.0 | 95.7 |

In Experiments 1-2, the cyanohydrin had an S to S + R ratio of about 92 and in Experiments 3-8 the ratio was 96.2

The invention claimed is:

1. A process for the preparation of gamma-cyhalothrin comprising steps of:
   a) chlorinating 1R cis-Z 3-(2-chloro-3,3,3-trifluoro-1-propenyl)-2,2-dimethyl cyclopropanecarboxylic acid to give 1R cis-Z 3-(2-chloro-3,3,3-trifluoro-1-propenyl)-2,2-dimethyl cyclopropanecarboxylic acid chloride;
   b) esterifying 1R cis-Z 3-(2-chloro-3,3,3-trifluoro-1-propenyl)-2,2-dimethyl cyclopropanecarboxylic acid chloride with the (S)-cyanohydrin of 3-phenoxy benzaldehyde (III) thereby to form a reaction mass including gamma-cyhalothrin and HCl;
   c) using a combination of physical methods and a sub-stoichiometric amount of a base to remove the HCl from said reaction mass.

2. A process according to claim 1 in which the base is added once the esterification reaction has been taken to greater than 50% completion using only physical removal of the HCl.

3. A process according to claim 1 in which the base is an organic base selected from pyridine, alkylpyridines, quinoline, the trimethylether of triethanolamine or the mono-hydrochloride salt of DABCO, or an inorganic base selected from an alkali metal carbonate or bicarbonate or alkaline earth metal oxide, hydroxide or carbonate or a combination of an organic and an inorganic base.

4. A process according to claim 3 in which the base is a pyridine or an alkylpyridine.

5. A process according to claim 1 in which the esterification reaction is carried out in a solvent selected from toluene, o-xylene, mixed xylenes or halobenzenes, for example fluorobenzene, hexane, cyclohexane, iso-hexane, heptane, octane or petroleum ethers.

6. A process according to claim 5 in which the solvent is hexane, cyclohexane, iso-hexane, heptane or octane.

7. A process according to claim 1 in which the esterification reaction is carried out in a two-phase system in which one phase is an aqueous phase, optionally containing an organic base.

* * * * *